United States Patent [19]

Martin

[11] Patent Number: 4,983,635

[45] Date of Patent: Jan. 8, 1991

[54] FORTIFIED QUATERNARY AMMONIUM COMPOUND WITH DUAL SYNERGISTIC PHENOLS

[76] Inventor: Howard Martin, 909 Pershing Dr., Silver Spring, Md. 20914

[21] Appl. No.: 243,088

[22] Filed: Sep. 12, 1988

[51] Int. Cl.$^5$ ............................................. A61K 31/14
[52] U.S. Cl. ................................................... 514/643
[58] Field of Search ................. 514/642, 643; 252/105

[56] References Cited

FOREIGN PATENT DOCUMENTS 8121204  7/1983  Japan ................................... 514/574

OTHER PUBLICATIONS

Chem. Abstract 84:17445a (1976), Washman et al.
Chem. Abstract 90:1014c (1978), Poli et al.
The Merck Index, Tenth Edition, p. 1043 (1983).
The Merck Index, Tenth Edition, p. 749 (1983).

Primary Examiner—Douglas W. Robinson
Assistant Examiner—Zohreh A. Fay
Attorney, Agent, or Firm—Walter G. Finch

[57] ABSTRACT

A fortified quaternary ammonium compound with dual synergistic phenols is provided for disinfection and sanitization. This formula consists of dual chain quaternary ammonium (N-alkyldimethylethylbenzyl ammonium chloride N-alkyldimethylbenzyl ammonium chloride), ortho phenyl phenol, paratertiary amyl phenol, isopropyl alcohol, citric acid, and water in the following gram proportions 47.70, 0.80, 0.80, 10.00, 0.40, 40.30, to give 100.00 grams total. This formula is the concentrated formulation and can be diluted for use in the health professions, consumers area, and agricultural area. The variant is decreased in the quaternary ammonium concentration from the concentrate of 25% to a low of 0.5%, all other compounds remain the same.

4 Claims, No Drawings

FORTIFIED QUATERNARY AMMONIUM COMPOUND WITH DUAL SYNERGISTIC PHENOLS

BACKGROUND AND SUMMARY OF THE INVENTION

This invention relates to proper infection control through mandatory chemical disinfection of instrumentation, and more particularly to a new formulation for disinfection and sanitization of surfaces, instruments, hospitals, and homes, convalescent and other similar material and the like.

Proper infection control, through chemical disinfection, of instrumentation is mandatory. In light of current knowledge, many compounds that were used in the past are no longer deemed acceptable. However, if these compounds were to be fortified and recombined into a new combination, rather than standing alone, the positive qualities would lead to a synergistic compound and then lead to a new useful efficacious disinfectant.

The most popular compound in use presently is glutaraldehyde. There are several drawbacks to glutaraldehydes in chemical disinfection usage. They are expensive, can only be diluted to a 0.5% if acid or 2% if alkaline. They are considered relatively toxic at 0.5% and toxic at 2% in handling They cause sever dermatitis and are allergenic. They have been shown to be unreliable in killing mycobacterium tuberculosis (TB). Some forms require heating to be effective and thereby give rise to noxious fumes The shelf life, once mixed, is not more than 30 days for the popular alkaline forms.

In contrast, quaternary ammonium compounds, alcohols and phenols have been studied and used for a long time and are inexpensive, less toxic and odorless Individually, phenols have been in disfavor and alcohols are merely mid level disinfectants. Quaternary ammonium compounds were used for disinfection for many years but certain limitations have caused them to fall into disuse.

However, QUATS possess a high surface activity. Natural water reduced their effectiveness and gram negative organisms were found to be resistant. This water problem is overcome by preparation with distilled water Irregular effectiveness against TB is overcome by the phenols and alcohols.

A new poly dual chain substituted quaternary ammonium compound has been found to be a more effective formulation but is still considered, if used alone, insufficient as a high level disinfectant. This poly dual chain, a homologous series of alkyl dimethyl ethyl benzyl ammonium chloride, has been shown to have the highest cidal efficiency against test organisms for approval by the U. S. Environmental Protection Agency.

Other positive qualities of QUATS are that they maintain activity against most gram positive organisms. They are less expensive than many other disinfectants. QUATS are relatively non-toxic and allergic reactions are rare and they are odorless. They do not cloud lensed instruments nor etch metal ones.

The QUATS have been used against viruses and have special properties against these organisms. They are very stable and have a long shelf like. Recent testing has indicated that a higher concentration of QUAT will inactivate gram negative organisms. QUATS will also behave as a surfactant enabling other compounds to penetrate microorganisms with greater effectiveness, thereby enhancing the secondary compounds cidal or killing effect.

Alcohols, as a group, possess many desirable features for a disinfectant. Its negatives have been quick evaporation and erratic cidal effects The positives are the cleaning action, bactericidal effects against vegetative organisms and are inexpensive.

Alcohols work by denaturing the proteins of the microorganisms. Pure alcohol is not as effective as mixtures of alcohol plus water It also interferes with cellular metabolism preventing cell division Isopropyl alcohol is the alcohol of choice due to lack of government restriction and also being the highest molecular weight alcohol miscible with water.

Isopropyl alcohol bactericidal effects are slightly greater than ethyl alcohol. Against mycobacterium tuberculosis, isopropyl alcohol was as effective as ethyl alcohol at one third the concentration. Isopropyl alcohol also is effective against lipophilic viruses.

The phenols were originally the standard disinfectant, but with improved compounds, they have not played a significant role. Overlooked have been the phenols effectiveness against certain microorganisms. These variations in their anti-bacterial behavior and toxicity have led to the development of synthetic compounds. Phenols act as protoplasmic poisons, penetrating and disrupting the cell wall and precipitating cell proteins Eventual cell death occurs from inactivation of essential enzyme systems.

Two new phenol derivations are ortho phenyl phenol and paratertiary amyl phenol. They have higher molecular weights and show a higher degree of bactericidal effectiveness and a decrease in toxicity. Ortho phenylphenol is approximately ten times more effective than standard phenol and is water soluble. It is also a fungicide and tuberculocide.

Paratertiary amylphenol is a high level bactericide but is relatively insoluble in water. If it can be solubilized and stabilized, it is 400 times as effective as standard phenol against gram positive and 50 times more effective against gram negatives as well as being a fungicide.

A properly formulated phenolic disinfectant made with synthetic detergents such as alkyl aryl sulfonate can be diluted with hard water and maintain complete clarity and germicidal activity The effect of pH is particularly noticeable when phenols are solubilized with sulfonates. Control of the pH, through the use of citric acid to develop an acidic solution, results in a highly efficient preparation of phenols with excellent disinfectant and detergent properties. Such a product will efficiently clean and disinfect in operation at a lower cost.

The development of a spray, squeeze bottle, or wipe is a logical extension of the formulation and would provide a simple means for use in small or difficult access areas. When sprayed or wiped wet, a surface is readily and conveniently disinfected. The properly formulated phenols are non-specific in regard to fungicidal and bactericidal action.

This new formulation allows the paratertiary amylphenol to remain in solution for up to two years. Phenolics have great value in specific areas. Improper combinations of phenols and anionic surfactants will show variations in cidal effects. The addition of alcohol and pH control and stabilize the formula and has been determined by experiment in order to give an acidic pH.

It is an object of this invention to provide a high level disinfectant that is reliable and economical to the health profession, industry, agriculture and consumer areas.

Another object of this invention is to combine the positive qualities of QUATS, alcohol, and phenols into a highly synergistic new solution that overcomes the weaknesses of the individual components.

And another object of this invention is to provide a new formulation for disinfection and sanitization which is concentrated and can be diluted for use in the health professions, consumer areas, and agricultural areas.

Even another object of this invention is to provide a fortified quaternary ammonium compound with dual synergistic phenols is provided.

And even another object of this invention is to provide a concentrated formulation in which the variant can be decreased in quaternary ammonium concentration from the concentrate of 25% to a low of 0.5%, with all other compounds remaining the same.

It is the purpose of this formulation to develop a high level, disinfectant that is reliable and inexpensive to the health professions, industry, agriculture and consumer areas The purpose of this new formulation is to combine the positive qualities of the aforementioned QUATS, alcohol, and phenols into a highly synergistic new solution that overcomes the weaknesses of the individual components.

The dual chain quaternary ammonium compounds +isopropyl alcohol +ortho phenylphenol +paratetiary amylphenol +citric acid +sodium alkyl arylsulfonate will give rise to a compound that is superior to the individual components, superior to older dual phenols and superior to glutaraldehydes.

Usage in a high concentration will enable ease of shipping, dilution as needed, no activation, low toxicity, and a wide range of cidal effects. In a high concentration, the compound can prevent proliferation of bacteria in injection water used in oil secondary recovery systems.

In proper concentrations, the new formulation will inhibit the sulfate reducing bacteria and pseudomonas species that contaminate the wells and holding tanks of oil systems. The compound can also be formulated as a solution properly concentrated for immersion of instruments, as a spray, as a wipe, as a solution to be activated in an ultrasonic bath.

A new formulation for disinfection and sanitization composed as following:

| | |
|---|---|
| Dual chain quaternary ammonium (N-Alkyldimethylethylbenzyl ammonium chloride N-alkyldimethylbenzyl ammonium chloride) | 47.70 grams |
| Ortho phenyl phenol | 0.80 grams |
| Para tertiary amyl phenol | 0.80 grams |
| Isopropyl alcohol | 10.00 grams |
| Citric acid | 0.40 grams |
| Water | 40.30 grams |
| TOTAL | 100.00 GRAMS |

This formula is the concentrated formulation and can be diluted for use in the health professions, consumers area, and agricultural area. The variant would be a decrease in the quaternary ammonium concentration from the concentrate of 25% to a low of 0.5%, all other compounds remain the same.

| | |
|---|---|
| Dual chain quaternary ammonium (N-Alkyldimethylethylbenzyl ammonium chloride N-alkyldimethylbenzyl ammonium chloride) | 25.00 grams |
| Ortho phenyl phenol | 0.80 grams |
| Paratertiary amyl phenol | 0.80 grams |
| Isopropyl alcohol | 10.00 grams |
| Citric acid | 0.40 grams |
| Water | 63.00 grams |
| TOTAL | 100.00 GRAMS |

A low concentrate will be as follows:

| | |
|---|---|
| Dual chain quaternary ammonium (N-Alkyldimethylethylbenzyl ammonium chloride N-alkyldimethylbenzyl ammonium chloride) | 0.50 grams |
| Ortho phenyl phenol | 0.80 grams |
| Paratertiary amyl phenol | 0.80 grams |
| Isopropyl alcohol | 10.00 grams |
| Citric acid | 0.40 grams |
| Water | 87.50 grams |
| TOTAL | 100.00 GRAMS |

The fortified quaternary ammonium compound can be used in the following areas:

1. Health Care—as an immersion solution for high level disinfection of instruments; as a spray to disinfect and sanitize inanimate surfaces; as a wipe to disinfect and sanitize inanimate surfaces; and as a high level detergent cleaner. Health care includes medical, dental, veterinary, hospital, podiatry, nursing, and convalescent care facilities.

2. Agricultural Areas—as a disinfectant, sanitizing detergent cleaner wash, spray and wipe on inanimate surfaces.

3. Consumer Areas—as a high level disinfectant sanitizer, detergent cleaner spray, wash and wipe for inanimate surfaces; for example, counter tops, toilet bowls and bathroom fixtures.

4. Industrial Areas—as a high level disinfectant sanitizer detergent cleaner for all inanimate surfaces.

5. Petroleum Industry—as a high level disinfectant, sanitizer, detergent cleaner for well head demulsification, drum reclammation, holding tank cleaning and disinfection, and reservoirs.

What is claimed is:

1. A new formulation for disinfection and sanitization, comprising,

| | |
|---|---|
| Dual chain quaternary ammonium (N-Alkyldimethylethylbenzyl ammonium chloride N-alkyldimethylbenzyl ammonium chloride) | 47.70 grams |
| Ortho phenyl phenol | 0.80 grams |
| Para tertiary amyl phenol | 0.80 grams |
| Isopropyl alcohol | 10.00 grams |
| Citric acid | 0.40 grams |
| Water | 40.30 grams |
| TOTAL | 100.00 GRAMS |

2. A new formulation for disinfection and sanitization, comprising,

| | |
|---|---|
| Dual chain quaternary ammonium (N-Alkyldimethylethylbenzyl ammonium Chloride N-alkyldimethylbenzyl ammonium chloride) | 25.00 grams |

| -continued | |
|---|---|
| Ortho phenyl phenol | 0.80 grams |
| Paratertiary amyl phenol | 0.80 grams |
| Isopropyl alcohol | 10.00 grams |
| Citric acid | 0.40 grams |
| Water | 63.00 grams |
| TOTAL | 100.00 GRAMS |

3. A new formulation for disinfection and sanitization comprising,

| | |
|---|---|
| Dual chain quaternary ammonium (N-Alkyldimethylethylbenzyl ammonium chloride) | 0.50 grams |
| Ortho phenyl phenol | 0.80 grams |
| Paratertiary amyl phenol | 0.80 grams |
| Isopropyl alcohol | 10.00 grams |
| Citric acid | 0.40 grams |

| -continued | |
|---|---|
| Water | 87.50 grams |
| TOTAL | 100.00 GRAMS |

4. A new formulation for disinfection and sanitization, comprising,

| | | |
|---|---|---|
| Dual chain quaternary ammonium (N-Alkyldimethylethylbenzyl ammonium chloride (N-alkyldimethylbenzyl ammonium chloride) | 25.00 | to 0.50 grams |
| Ortho phenyl phenol | 0.80 | 0.80 grams |
| Paratertiary amyl phenol | 0.80 | 0.80 grams |
| Isopropyl alcohol | 10.00 | 10.00 grams |
| Citric acid | 0.40 | 0.40 grams |
| Water | 63.00 | 87.50 grams |
| TOTAL | 100.00 | 100.00 GRAMS |

* * * * *